United States Patent [19]

Falk

[11] Patent Number: 4,994,024
[45] Date of Patent: Feb. 19, 1991

[54] ARTHROSCOPY HOOK-CLIPPERS

[75] Inventor: Ernst Falk, Sternenfels-Diefenbach, Fed. Rep. of Germany

[73] Assignee: Richard Wolf GmbH, Fed. Rep. of Germany

[21] Appl. No.: 381,981

[22] Filed: Jul. 19, 1989

[30] Foreign Application Priority Data

Jul. 22, 1988 [DE] Fed. Rep. of Germany ....... 3824910

[51] Int. Cl.$^5$ .............................................. A61B 17/00
[52] U.S. Cl. ..................................... 604/22; 128/752; 606/83
[58] Field of Search ................................ 128/749–751, 128/752; 604/22; 606/83, 167, 170, 205, 207, 198, 171; 30/133

[56] References Cited

U.S. PATENT DOCUMENTS

| | | | |
|---|---|---|---|
| 2,751,908 | 6/1956 | Wallace | 128/321 |
| 2,790,437 | 4/1957 | Moore | 606/170 |
| 4,084,594 | 4/1978 | Mosior | 606/170 |
| 4,522,206 | 6/1985 | Whipple et al. | 128/312 |
| 4,662,371 | 5/1987 | Whipple et al. | 128/312 |

FOREIGN PATENT DOCUMENTS 8528482 10/1985 Fed. Rep. of Germany.
3526822 2/1987 Fed. Rep. of Germany.

*Primary Examiner*—C. Fred Rosenbaum
*Assistant Examiner*—William W. Lewis

[57] ABSTRACT

Arthroscopy hook-clippers comprise a circular cross-section outer shaft having at a distal end thereof a fixed jaw and a movable jaw pivoted to the fixed jaw. Within the shaft are a thrust rod which is movable axially thereof to pivot the movable jaw with respect to the fixed jaw, and beside the thrust rod, a vacuum extraction channel. The extraction channel is of substantially circular cross-section excepting that it has a flat upper wall, which co-operates with the upper internal wall of the shaft to define a guideway for the thrust rod the cross-section of which is matched to that of the guideway.

5 Claims, 2 Drawing Sheets

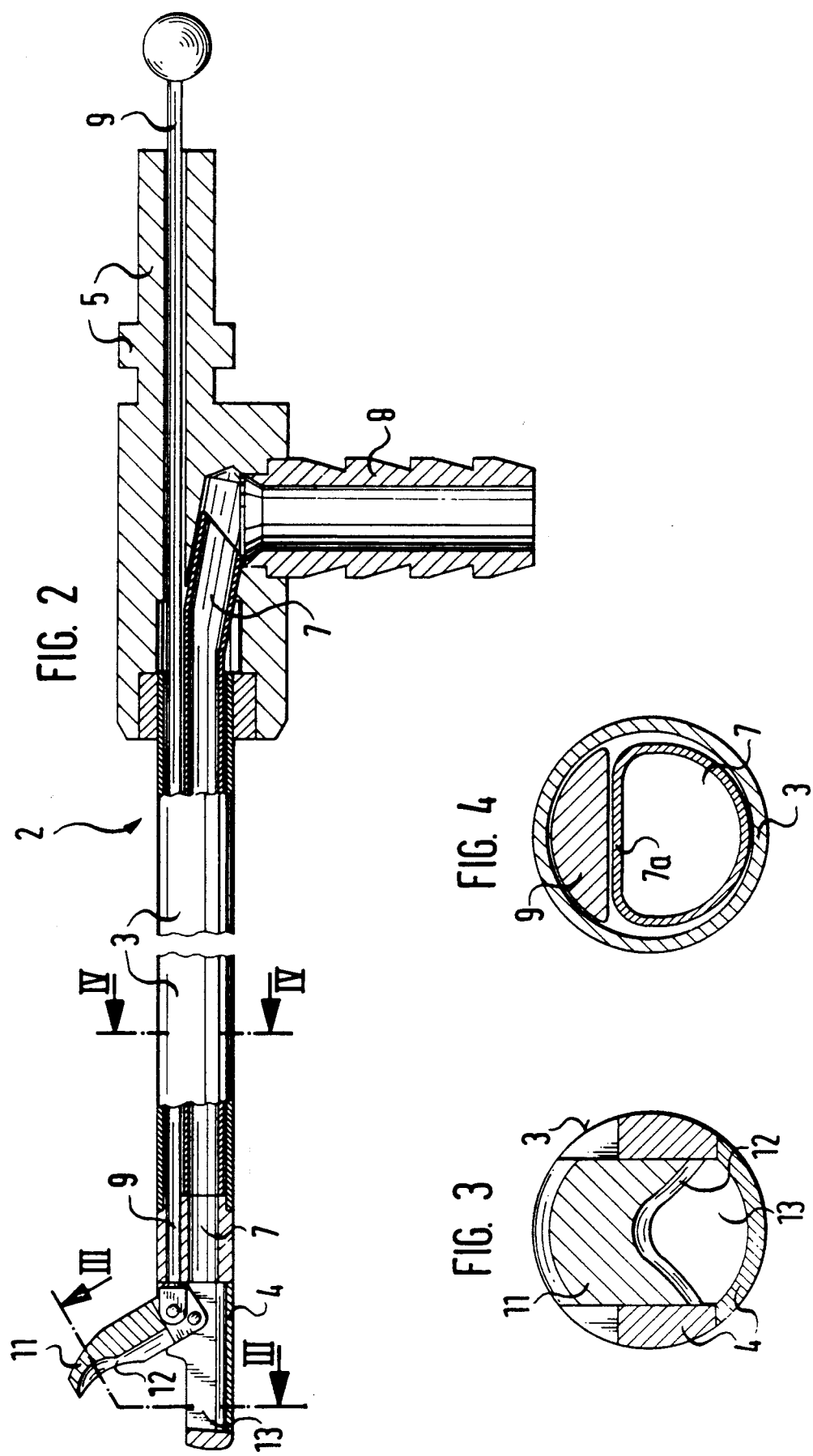

ARTHROSCOPY HOOK-CLIPPERS

FIELD OF THE INVENTION

This invention relates to arthroscopy hook-clippers comprising a fixed clipper jaw formed by the distal end of a circular cross-section outer shaft and a movable hooked jaw which is pivotally displaceable with respect to the fixed jaw by means of a thrust rod which is in turn axially displaceable by means of a scissors type handle and extends through the outer shaft beside a flushing or vacuum extraction channel, in parallel relationship therewith.

BACKGROUND OF THE INVENTION

Such hook-clippers, which are described in DE-A-3526822, have the disadvantage that in use, the thrust rod comes into direct contact with clipped away pieces of tissue or bone which are to be extracted by suction or with soiled flushing or vacuum extraction fluid, so that the spread of bacteria as well as inhibition of the vacuum extraction operation can occur, with undesirable results.

SUMMARY OF THE INVENTION

An object of the invention is to provide arthroscopy hook-clippers in which, such proliferation of bacteria is avoided, the vacuum removal operation is unobstructed and the diameter of the outer shaft is kept as small as possible, whilst the thrust rod is capable of transmitting considerable force to the movable jaw.

Another object of the invention is to ensure the unobstructed extraction of the cartilage or bone pieces removed by the hook-clippers through said channel, even when the jaws are closed.

A further object of the invention is to provide hook-clippers which are compatible with scissors type handles of the kind which are usually available in hospitals or in private medical practices.

According to the invention the flushing and vacuum extraction channel, which extends through the circular cross-section outer shaft, communicates with a deep inner recess in the movable hooked jaw, and is of substantially circular cross-section excepting that it has a flat upper wall facing the thrust rod, the upper internal surface of the shaft co-operating with said flat upper wall to define a guideway for the thrust rod which has a cross-section matched to that of said guideway.

The outer shaft, through which said channel extends, may be provided with a stub connector extending at an angle laterally therefrom, near its proximal end. THe outer shaft is releasably connectable to a fixed arm of said scissors type handle by means of a coupling element, the proximal end of said thrust rod is releasably connectable to a pivotable arm of said handle and the distal end of said thrust rod is articulated to said movable jaw.

BRIEF DESCRIPTION OF THE DRAWINGS

FIG. 2 is a side view shown mainly in longitudinal section, of the attachment; and FIGS. 3 and 4 are cross-sectional views taken on the lines III—III and IV—IV, respectively, of FIG. 2.

DETAILED DESCRIPTION OF THE INVENTION

Figure 1:
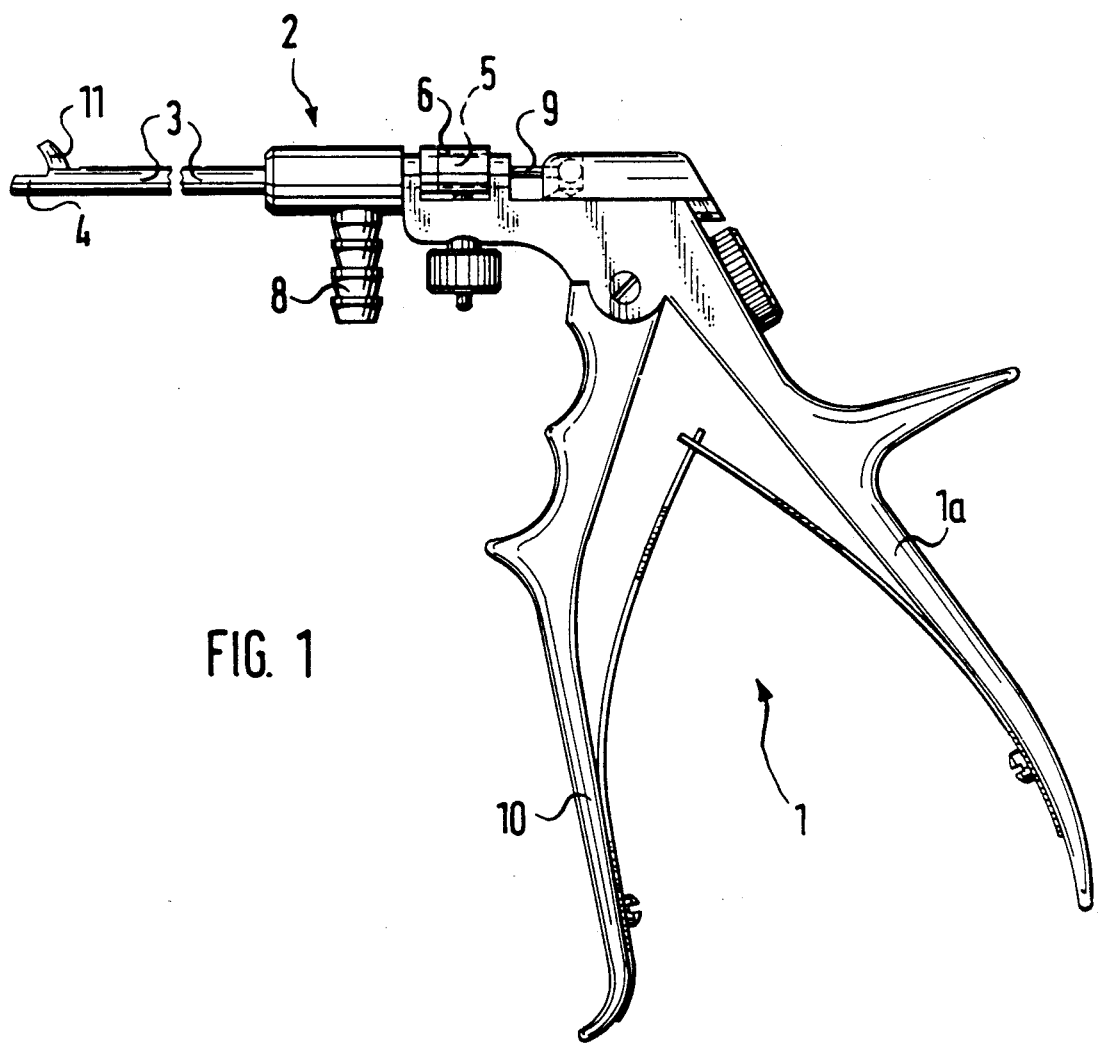
FIG. 1 is a side view of arthroscopy hook-clippers, comprising a clipper attachment and a forceps handle.

The arthroscopy hook-clippers comprise a clipper attachment 2 arranged to be coupled to a forceps handle 1 which may be of a kind which is usually available in a hospital or in a private medical practice, for use with known attachments.

The attachment 2, which may differ in its dimensions, comprises a circular cross-section outer shaft 3 having a distal end formed with a fixed clipper jaw 4. The shaft 3 has at its proximal end, a male coupling element 5 for exchangeable connection to a fixed arm 1a of the handle 1 by means of a female coupling element 6, which is provided with a locking screw.

A flushing or vacuum extraction channel 7 (FIGS. 2 and 4) extends through the shaft 3 and is provided with a stub connector 8 which is arranged at right angles to the shaft 3 and is positioned distally of a pivotable arm 10 of the handle 1 for connection to a vacuum source (not shown). The channel 7 is a tube of substantially circular cross-section but is surmounted by a flat upper wall 7a as shown in FIG. 4.

As best seen in FIG. 4, the wall 7a and the upper internal part of the shaft 3 define a sealing guideway snugly receiving a thrust rod 9 of complementary cross-section matched to said guideway. The flat upper wall 7a of the channel faces a flat lower surface of the thrust rod 9 as best seen in FIG. 4.

The thrust rod 9 is pivotally attached at its distal end to a hooked movable clipper jaw 11, which is pivoted to the fixed jaw 4. When the proximal end of the rod 9 is connected to the pivotable arm 10 of the handle 1, as shown in FIG. 1, the rod 9 allows, by virtue of its cross-section, very substantial forces to be transmitted from the arm 10 to the jaw 11. The shaft 3 may accordingly be of small external diameter, with the channel 7 being comparatively wide. The jaw 11 has a deep inner or lower recess 12 for receiving any clipped away pieces of bone or tissue. The jaw 4 has an inner or upper recess 13 to which the channel 7 is directly connected so that said pieces can be extracted therethrough by means of said vacuum source in the closed position of the jaws 4 and 11.

For optimum vacuum extraction in the area of the cutting edges of the jaws 4 and 11, the distal end of the thrust rod 9 and the proximal end of the jaw 11 are snugly interengaged in the region of their articulated connection so that the extraction of flushing fluid is effectively prevented in that region.

What is claimed is:

1. Arthroscopy hook-clippers comprising: a hollow outer shaft having a circular cross-section, a proximal end and a distal end; a fixed jaw being formed by the distal end of said shaft; a movable hooked jaw being pivoted to said shaft at the distal end thereof; a thrust rod extending through said shaft and being axially movable for pivotally displacing said movable jaw with respect to said fixed jaw, by means of a scissors type handle for said hook-clippers; and a hollow tube forming a flushing or vacuum extraction channel extending through said outer shaft beside said thrust rod, said tube communicating with a deep inner recess in said fixed jaw and having a substantially circular cross-section excepting that the tube has a flat upper wall facing said thrust rod and said flat upper wall defining in cooperation with an upper internal wall surface of said outer shaft a guideway for said thrust rod, said thrust rod having a cross-section which is matched to a cross-section of the guideway.

2. Arthroscopy hook-clippers according to claim 1, wherein said tube has at its proximal end, a stub connector projecting laterally therefrom and at an angle thereto, coupling means being provided for releasably connecting said outer shaft to a fixed arm of said scissors type handle and the proximal end of said thrust rod to a pivotable arm of said handle, said thrust rod being articulated to said movable jaw.

3. An arthroscopy hook-clipper comprising: a scissor-type handle; an outer hollow shaft having a circular cross-section with a proximal end and a distal end; means for connecting the proximal end of the shaft to the scissor-type handle; a fixed jaw having a deep inner recess and being formed at he distal end of said shaft; a movable jaw having a deep inner recess being mounted for pivotal movement at the distal end of the shaft with respect to said fixed jaw; a tube extending through the interior of said shaft having a distal end in communication with both of the deep inner recesses of the jaws and having a proximal end in communication with a fitting for connecting said tube to a source of fluid, said tube having a substantially circular cross section with a flat wall, said flat wall coacting with an inner surface of the shaft to define a guideway extending the length of said shaft; a thrust rod extending through said guideway having a distal end connected to the movable jaw and a proximal end having means for connecting the rod to said scissor-type handle so the actuation of said handle causes axial movement of the thrust rod to displace the movable jaw with respect to said fixed jaw.

4. An arthroscopic hook-clipper according to claim 3, wherein the thrust rod has a cross-section with a curved surface merging with a flat surface, said cross-section of the thrust rod substantially filling the cross-section of the guideway.

5. An arthroscopic hook-clipper according to claim 4, wherein both the means connecting the proximal end of the shaft to said scissor-type handle and the means connecting the proximal end of the rod provide a detachable connection.

* * * * *